United States Patent [19]

Lee

[11] Patent Number: 5,628,891

[45] Date of Patent: May 13, 1997

[54] ELECTROPHORESIS DEVICE

[75] Inventor: Richard K. Lee, Chunghua, Taiwan

[73] Assignee: AAT Laboratories, Inc., Upland, Calif.

[21] Appl. No.: 568,190

[22] Filed: Dec. 6, 1995

[51] Int. Cl.$^6$ .......................... G01N 27/26; G01N 27/447
[52] U.S. Cl. .......................... 204/612; 204/461; 204/466; 204/616
[58] Field of Search ..................................... 204/461, 612, 204/456, 457, 458, 459, 462, 463, 464, 465, 466, 467, 468, 469, 470, 606, 607, 608, 609, 610, 613, 614, 615, 616, 617, 618, 619, 620, 621

[56] References Cited

U.S. PATENT DOCUMENTS

| | | | |
|---|---|---|---|
| 4,427,294 | 1/1984 | Nardo | 356/344 |
| 4,930,893 | 6/1990 | Manian | 356/344 |
| 5,171,534 | 12/1992 | Smith et al. | 422/82.05 X |
| 5,192,412 | 3/1993 | Kambara et al. | 204/612 |

OTHER PUBLICATIONS

Bio–Rad product brochure, *Nucleic Acid Electrophoresis—Nucleic Acid Sequencing*, "GS Gene Loader II Automated Gel Loading System", p. 211, (no date available).

Pharmacia product brochure, "Automated Laser Fluorescent A.L.F. DNA Sequencer™", pp. 1–12, No Month Available 1990.

Applied Biosystems product brochure, *373 DNA Sequencer*, "Automated Sequencing, Sizing, and Quantitation", No Month Available 1994.

Perkin Elmer product brochure, "377 DNA Sequencer", No Month Available 1994.

*Primary Examiner*—Kathryn L. Gorgos
*Assistant Examiner*—John S. Starsiak, Jr.
*Attorney, Agent, or Firm*—Fish & Richardson P.C.

[57] ABSTRACT

An electrophoresis gel carrier includes end mounts, each having a buffer well and retainer elements constructed to support an electrophoresis medium gel so that the gel is in communication with the buffer well. Each end mount includes a base plate which defines the buffer well as well as a lower retainer element. Each end mount also includes an upper retainer element which when aligned with the lower retainer defines an opening in fluid communication with the buffer well. The openings in each of the end mounts receive opposite ends of the electrophoresis medium gel so that the gel is in communication with the buffer well. An apparatus is provided which allows a number of electrophoresis gels, mounted in gel carriers, to be analyzed using a single detector.

13 Claims, 7 Drawing Sheets

ELECTROPHORESIS DEVICE

BACKGROUND OF THE INVENTION

Advanced nucleic acid sequencing technology was introduced in the 1980's as an improved technology in the study of molecular biology. Among others, U.S. Pat. Nos. 5,171,534, 4,811,218 and 5,192,412 disclose the basic principles and some preferred embodiments of electrophoresis apparatus and/or systems.

In U.S. Pat. No. 5,171,534, a column type gel is disclosed to perform the electrophoresis process. In the disclosed process, chromophores or fluorophores are used to tag the DNA fragments produced by the sequencing chemistry and permit the detection and characterization of the fragments as they are resolved by electrophoresis through the gel. The detection disclosed employs an absorption or fluorescent photometer capable of monitoring the tagged bands as they are moving through the gel.

In U.S. Pat. No. 4,811,218, a flat panel type gel is disclosed to perform the electrophoresis process of many samples at the same time. The disclosed system includes an optical system and a translational stage for mounting the optical system and for moving the optical system in a direction parallel to the planar array of electrophoresis lanes in order to move a collection element to receive radiation from different lanes, one lane at a time.

The above two types of electrophoresis apparatus tag four different fluorescence molecular to four DNA fragments terminating with A,T,C, and G respectively. The technology disclosed makes the electrophoresis process possible by using a single electrophoresis lane instead of the conventional four lanes. Furthermore, these electrophoresis apparatus avoid the need for providing multiple injections for samples with long DNA molecule.

In U.S. Pat. No. 5,192,412, lengthwise grooves are formed in one surface of a plane plate serving as a capillary electrophoresis path. A widthwise groove intersecting the lengthwise grooves is provided for the passage of a light beam.

However, even with the technology of the state of art, the electrophoresis process for large number of samples is still time consuming.

SUMMARY OF THE INVENTION

The invention features an electrophoresis gel carrier for supporting an electrophoresis gel. The gel carrier includes end mounts, each having an upper retainer and a base plate defining a lower retainer. The upper retainer is aligned and configured to couple with the lower retainer of the base plate. The lower and upper retainers define a buffer well for supporting a buffer solution. The end mounts receive opposite ends of the electrophoresis medium gel so that the gel is in fluid communication with the buffer well.

The base plate may include partitions adapted to divide the buffer well into discrete sample well cells, each individual sample well cell receiving one or the other of the ends of the gel. In some embodiments, the mounts may include a buffer reservoir in fluid communication with each of the sample well cells. Alternatively, the gel carrier may include a buffer tank in which the electrophoresis medium gel and the end mounts are placed. The electrophoresis gel carrier may include a reflective mirror disposed along a lateral edge of the gel and configured to redirect light from an external source through the gel.

In one embodiment, the electrophoresis medium gel is in the form of capillary tubes. In this arrangement, the lower retainer includes a plurality of lower concave surfaces, and the upper retainer plate includes a plurality of upper concave surfaces in alignment with the lower concave surfaces. Each of the aligned upper and lower concave surfaces define an aperture which opens into the buffer well and receives a second end of the capillary tube.

In another embodiment, the electrophoresis medium gel is in the form of a slab with the openings in the mounts defining slots for receiving respective ends of the electrophoresis medium gel. The slab gel may be received in the slot so that sample lanes in the slab gel communicate with the sample well cells.

In another aspect of the invention, an apparatus is provided for performing, using a single detector, electrophoresis processes of a large number of samples disposed within individual gel carriers. The apparatus includes a plurality of electrophoresis gel carriers, each carrier supporting an electrophoresis gel, and a detector configured to acquire information from the individual electrophoresis gel carriers and transmit the information to a data collector. The apparatus further includes a conveyor which moves at least one of the detector and carriers with respect to each other to allow the detector to acquire the information in a predetermined sequence. The predetermined sequence is selected so that the detector acquires information from each of the gels at known time intervals.

Preferred embodiments of the invention may include one or more of the following features. The apparatus includes a platform adapted to support the electrophoresis gel carriers and resident positions formed by the platform and conveyor. In one embodiment, the gel carriers are supported at stationary positions of the platform and the detector moves to the stationary positions to acquire information from each of the gels. The resident positions include at least one imaging position where the detector, in a predetermined sequence, acquires information from each gel at the predetermined time intervals. The resident position also includes storage positions where the carriers reside when information is not being acquired from a given carrier. The apparatus may include a conveyor which moves the carriers between imaging and storage positions. The imaging and storage positions may be coplanar. In one embodiment, the conveyor rotates to move each of said carriers from their respective storage positions to said at least one imaging position.

The apparatus further includes a buffer withdraw/injection device in communication with a buffer storage tank for withdrawing used buffer from the carriers and injecting new buffer. The apparatus further includes a sample injector for adding sample to the carriers and a data collector/controller for automatically controlling the apparatus. The detector may be, for example, a charge coupled device (CCD) camera, a diode array, or a laser beam measurement instrument.

The gel carrier may be any gel carrier including ones having the structures described above, as well as other conventional gel carriers known in the art.

In another aspect of the invention, a method for performing a number of electrophoresis processes includes the following steps:

a) supporting a plurality of electrophoresis gels on individual gel carriers in fluid communication with buffer solution, b) positioning each gel carrier at storage positions of a platform, c) conveying each of the gel carriers, in a predetermined sequence, to an imaging position of the platform, d) illuminating the electrophoresis gels at the imaging position, e) acquiring, at the imaging position, information from the electrophoresis gel carrier, and f) transmitting the information to a data collector.

In preferred embodiments, the method may include one or more of the following steps. The imaging position may be fixed with the detector disposed at the imaging position and the conveying step comprises conveying each of the gel carriers to the imaging position where the detector is disposed at a fixed position and, after step f), the gel carrier is conveyed to one of the storage positions. After step f), the gel carrier may be conveyed to its original storage position. Steps c) through f) may be repeated at predetermined time intervals. In addition, the process may further include the steps of withdrawing used buffer solution from each of the gel carriers and reinjecting fresh buffer solution into the gel carriers. The step of illuminating the electrophoresis gel includes scanning each electrophoresis gel with a laser.

Other features and advantages of the invention will become apparent from the following drawings and detailed description, and also from the claims.

DETAILED DESCRIPTION OF THE INVENTION

Figure 1:
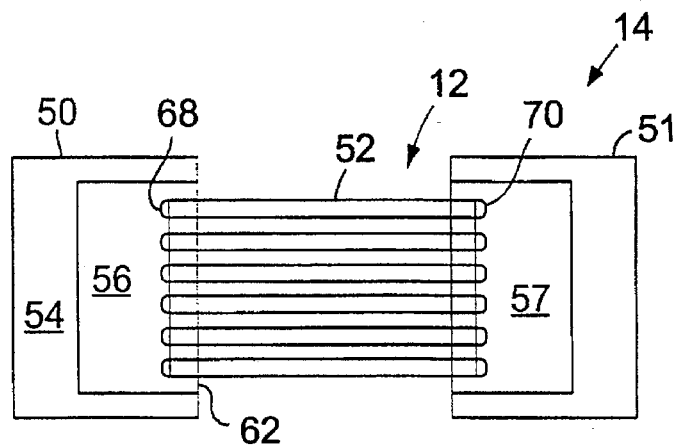
FIG. 1 is a top view of a gel carrier according to the invention.

Referring to FIG. 1, a gel carrier 14 includes two end mounts 50, 51 supporting an electrophoresis gel 12 disposed within capillary tubes 52 formed of, for example, glass. Gel 12 generally includes many capillary tubes, however, for purposes of clarity, only six tubes are shown here.

Figure 1A:
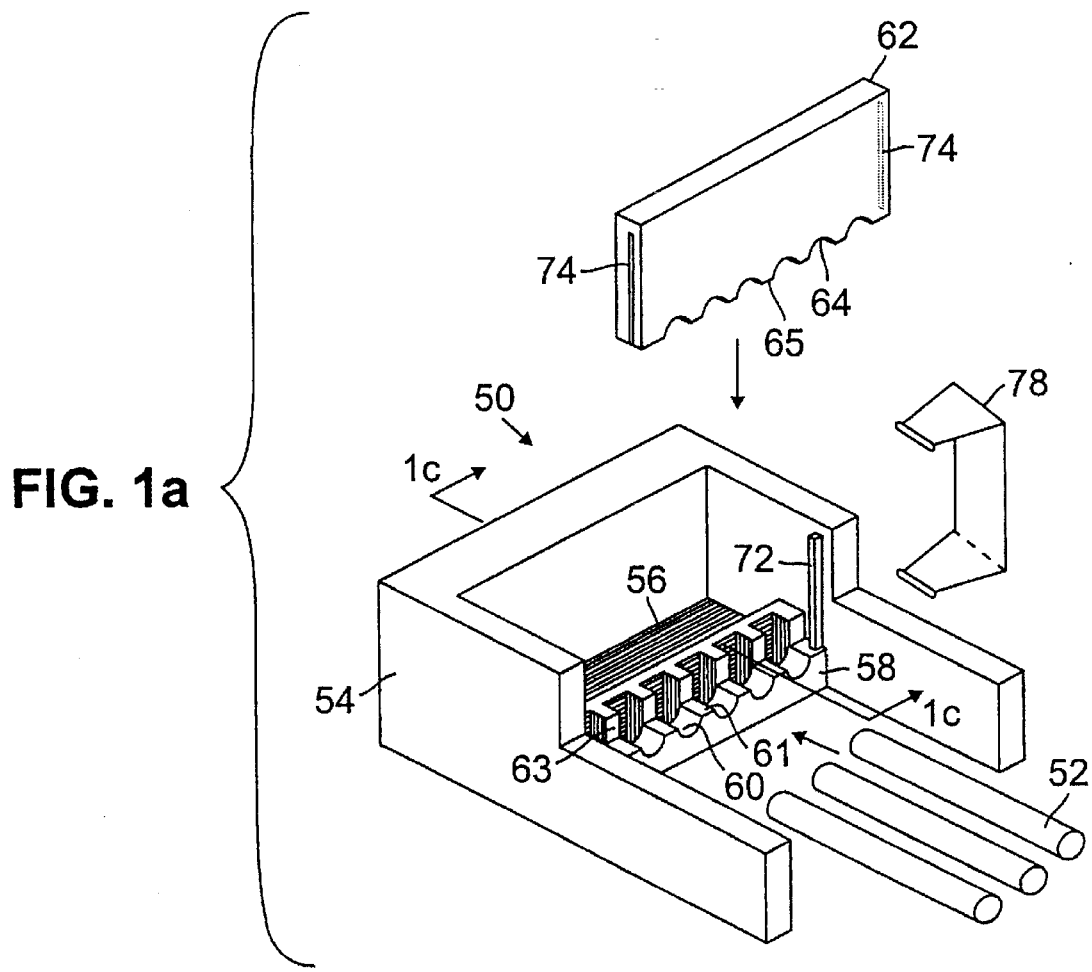
FIG. 1a is a diagrammatic representation of the gel carrier of FIG. 1.
Figure 1B:
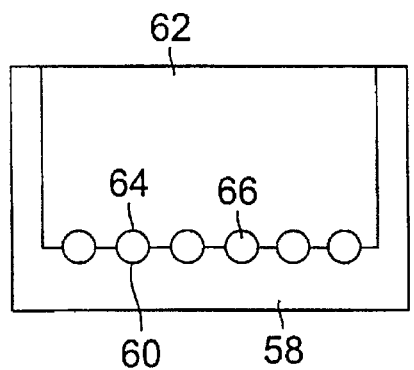
FIG. 1b is a front view of the gel carrier of FIG. 1.
Figure 1C:
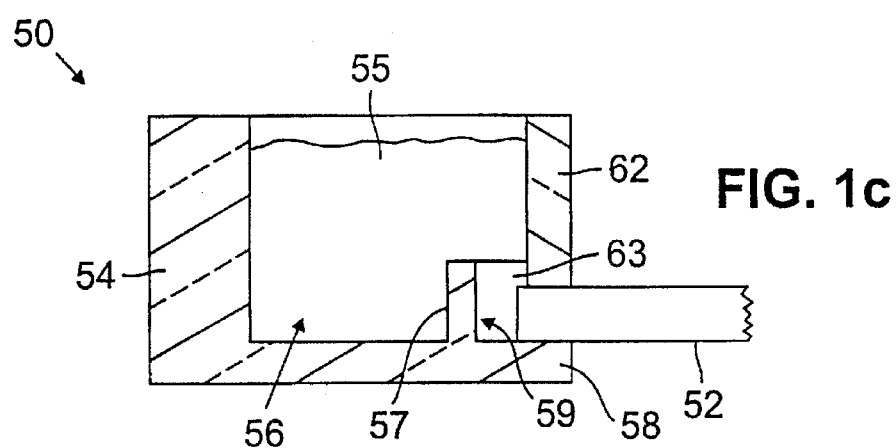
FIG. 1c is a cross-sectional side view of the gel carrier of FIG. 1a along lines 1c—1c.

Referring to FIGS. 1a, 1b, and 1c, end mount 50 includes a base plate 54 defining a buffer reservoir 56 for supporting electrophoresis buffer solution 55. Formed within base plate 54 is a lower retainer 58 having a plurality of lower concave surfaces 60 and lower shelves 61. An upper retainer 62 having a plurality of upper concave surfaces 64 and upper shelves 65 is slidably received within base plate 54 to mate with lower retainer 58, thereby providing one of the walls of buffer reservoir 56. Guide members 72 formed within side walls of base plate 54 engage slots 74 formed along outer edges of upper retainer 62. At least one clamp 78 is used to hold the lower and upper retainers together. As shown particularly in FIG. 1b, lower and upper concave surfaces 60 and 64 define apertures 66 which open into buffer reservoir 56.

Referring to FIG. 1c, base plate 54 includes a vertically extending separation wall 57 which, in conjunction with the lower and upper retainers, define individual sample wells 59. Each sample well is separated from an adjacent sample well by a cell partition 63 formed on separation wall 57 and by the mating of the lower and upper shelves of the retainers. Each sample well 59 supports buffer solution from buffer reservoir 56.

Referring again to FIG. 1, a first end 68 of capillary tube 52 is received in an aperture in first end mount 50 and extends into its associated sample well 59 with a second end 70 of capillary tube 522 received in an aperture in second end mount 51 having buffer reservoir 57. Electrical wires 26 (FIG. 5) leading to a power supply (not shown) are electrically connected to buffer reservoirs 56, 57 for providing an electrophoresis electric field in each of capillary tubes 52.

Figure 2:
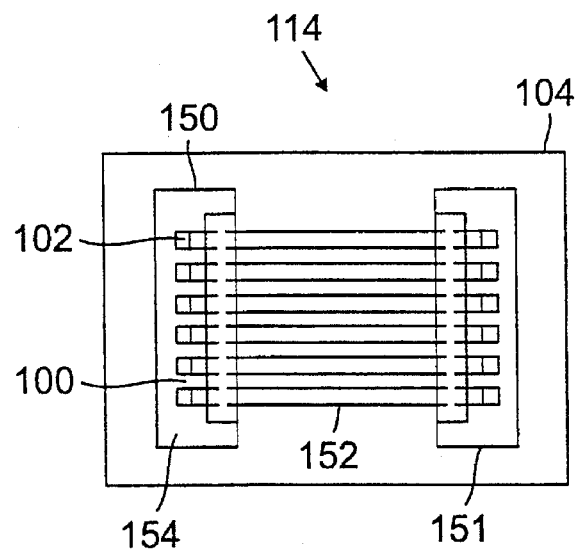
FIG. 2 is a top view of a second embodiment of a gel carrier according to the invention.
Figure 2A:
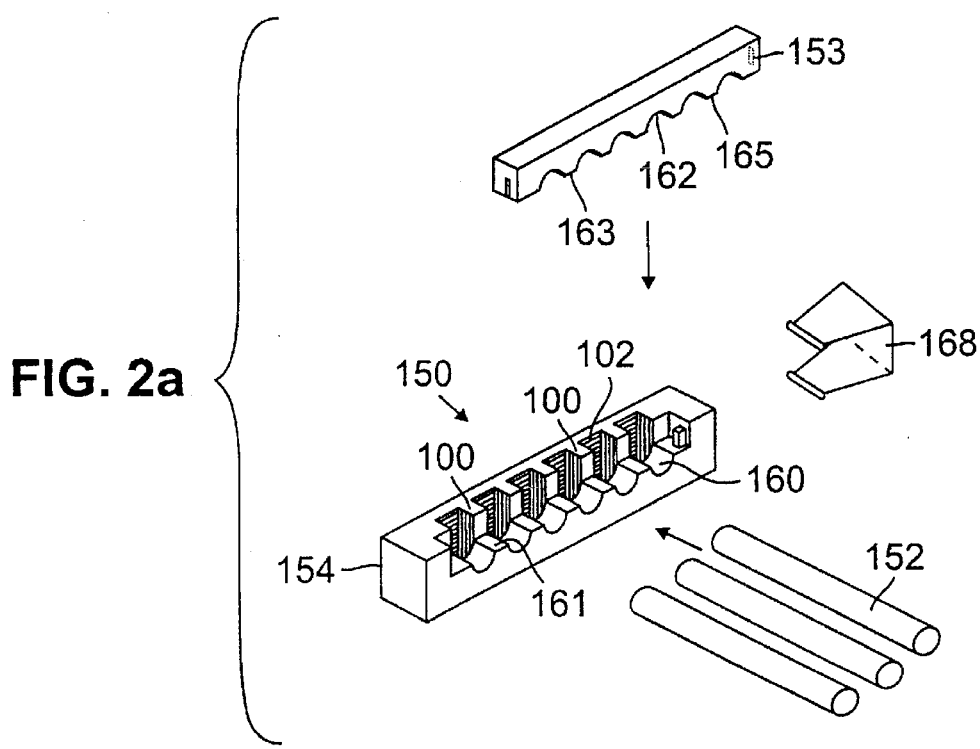
FIG. 2a is a diagrammatic representation of the gel carrier of FIG. 2.
Figure 2B:
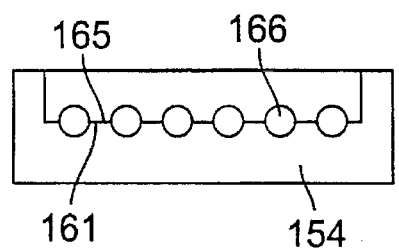
FIG. 2b is a front view of the gel carrier of FIG. 2.

Referring to FIGS. 2, 2a, and 2b, another embodiment of a gel carrier for performing an electrophoresis process is shown. As shown in FIG. 2, a carrier 114 includes end mounts 150, 151 for supporting capillary tubes 152. End mount 150 includes a base plate 154 having a plurality of lower concave surfaces 160, lower shelves 161 and individual cell partitions 100 which divide base plate 154 into discrete sample well cells 102. An upper retainer 153 having upper concave surfaces 162 and upper shelves 163 is received within base plate 154 to provide apertures 166 which open into sample well cells 102. Shelves 161 and 163 are aligned with cell partitions 100 and mate with each other to form a sealed contact. Clamp 168 secures the lower and upper retainers together. Carrier 114 further includes a buffer tank 104 (FIG. 2) containing a buffer solution in which the gel carrier 114 is placed.

Figure 3:
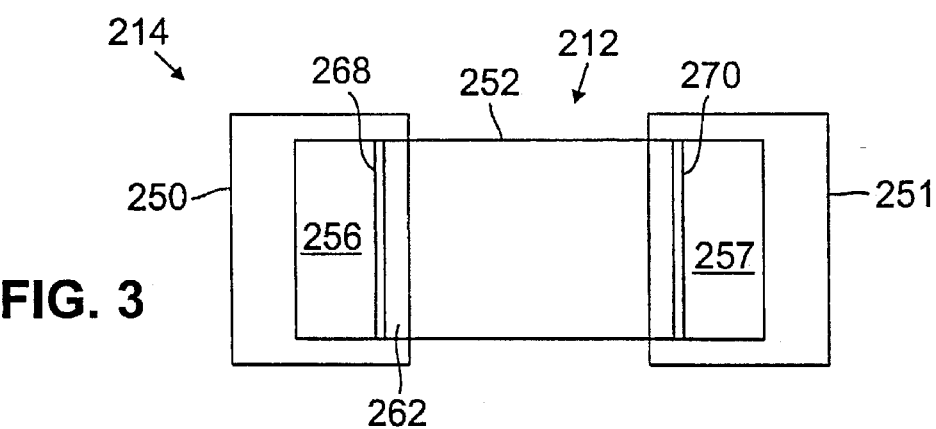
FIG. 3 is a top view of a third embodiment of a gel carrier according to the invention.
Figure 3A:
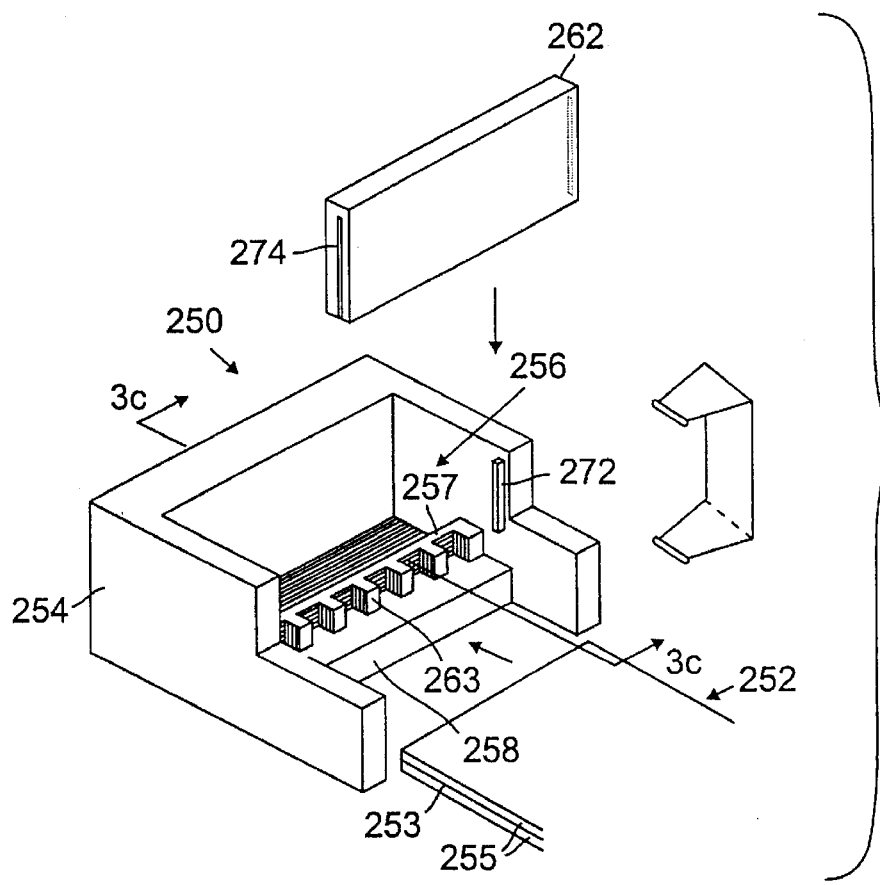
FIG. 3a is a diagrammatic representation of the gel carrier of FIG. 3.
Figure 3B:
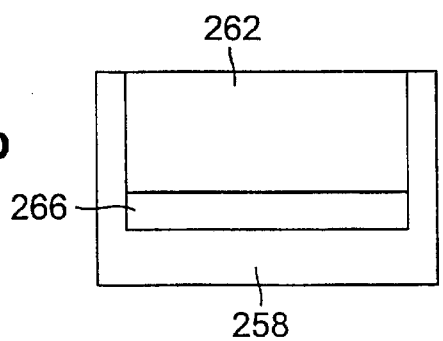
FIG. 3b is a front view of the gel carrier of FIG. 3.

In a further embodiment, a gel carrier used with electrophoresis gel in the form of a slab is shown. Referring to FIGS. 3, 3a, 3b, and 3c, a gel carrier 214 includes two end mounts 250, 251 supporting an electrophoresis gel 253. Electrophoresis gel 253 is supported between a pair of glass plates 255 to provide a slab gel 252. As shown particularly in FIG. 3a, end mount 250 includes a base plate 254 and a lower retainer 258. Base plate 254 defines a buffer reservoir 256 containing electrophoresis buffer solution 255. End mount 250 further includes an upper retainer 262 aligned with lower retainer 258. Guides 272 formed along inner sidewalls of base plate 254 slidably receive slots 274 in upper retainer 262. At least one clamp 278 is used to hold the lower and upper retainers together. Lower and upper retainers 258, 262 define a slot 266 (FIG. 3b). As shown in FIG. 3, a first end 268 of slab gel 252 is received in the slot in first end mount 250 and extends into buffer reservoir 256. A second end 270 of the slab gel 252 is received in the slot of second end mount 251 and extends into buffer reservoir 257.

Figure 3C:
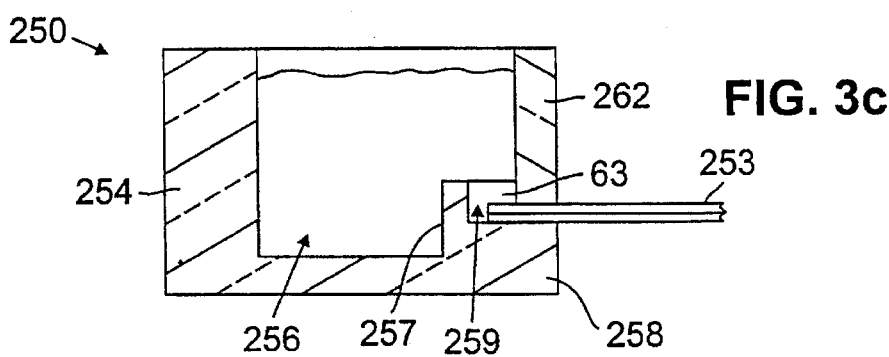
FIG. 3c is a cross-sectional side view of the gel carrier of FIG. 3a along lines 3c—3c.

As shown particularly in FIG. 3c, a separation member 257 extending vertically from a rear portion of lower retainer 258 includes cell partition walls 263, which, in conjunction with retainer walls 258, 262, define individual sample wells 259. As was the case in the embodiment of FIG. 1, sample wells 259 support buffer solution from buffer reservoir 256.

Figure 4:
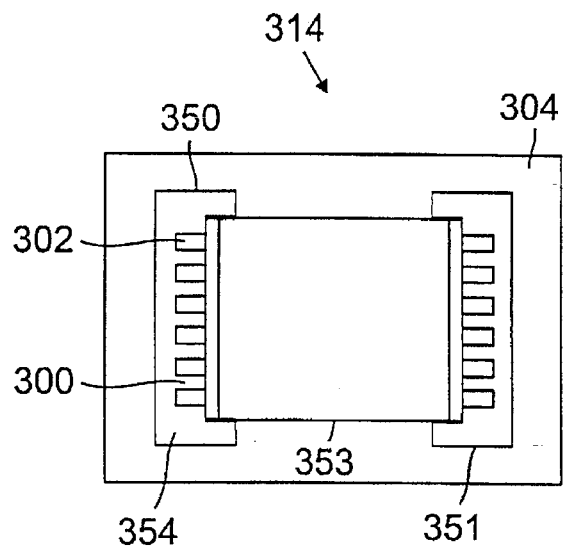
FIG. 4 is a top view of a fourth embodiment of a gel carrier according to the invention.
Figure 4A:
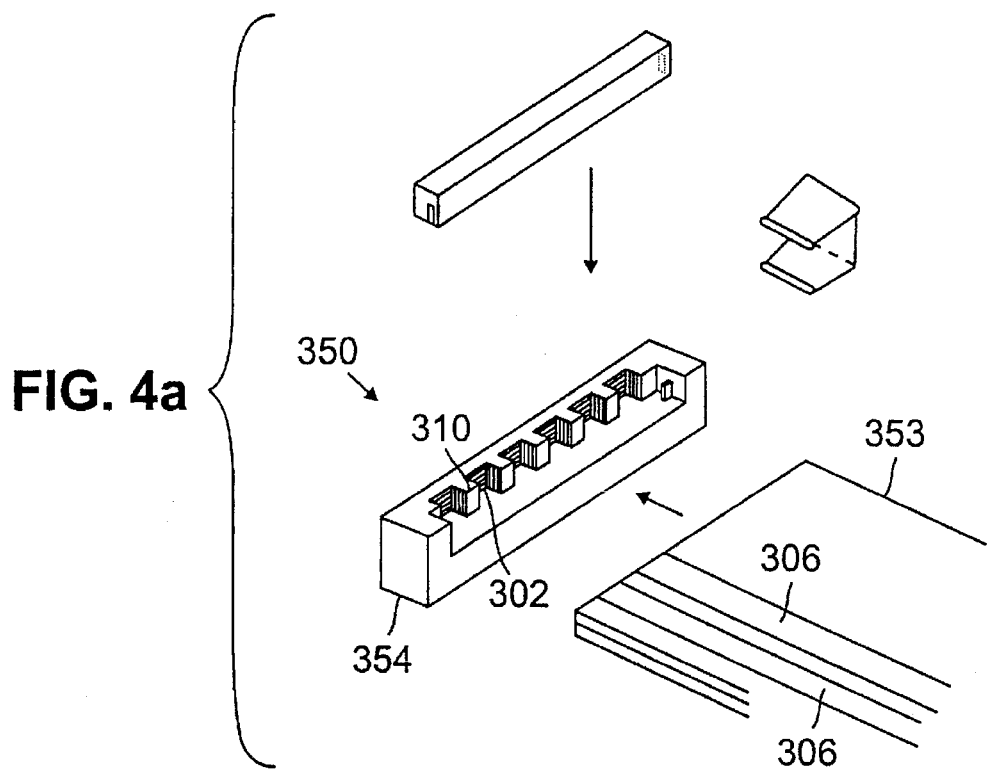
FIG. 4a is a diagrammatic representation of the gel carrier of FIG. 4.
Figure 4B:
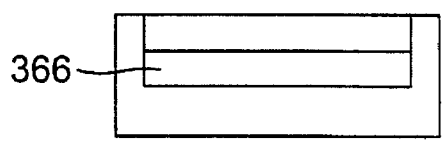
FIG. 4b is a front view of the gel carrier of FIG. 4.

Referring to FIGS. 4, 4a, and 4b, in still another embodiment, a carrier 314 is shown in which base plate 354 of end mount 350 includes a plurality of cell partitions 300 separating discrete sample well cells 302. Slab gel 353 is received in slot 366 (FIG. 4b) such that each of a plurality of sample lanes 306 in slab gel 353 extend into one of sample well cells 302. Carrier 314 includes a tank 304 containing buffer solution and in which the gel held in end mounts 350, 351 is placed.

It is important to note that in the embodiments described in conjunction with FIGS. 1, 1a, and 1b and FIGS. 3, 3a, and 3b, the buffer reservoirs 56, 256 serve the same purpose as the buffer tanks 104, 304 described in conjunction with FIGS. 2, 2a and 2b and FIGS. 4, 4a, and 4b. Moreover, it is also appreciated that the pair of end mounts for each of the above embodiments need not be the same. It is generally required that only one of the pair of end mounts include individual sample wells. The other of the pair of end mounts need only ensure that the end(s) of the gel(s) be in communication with electrophoresis buffer solution.

Figure 5:
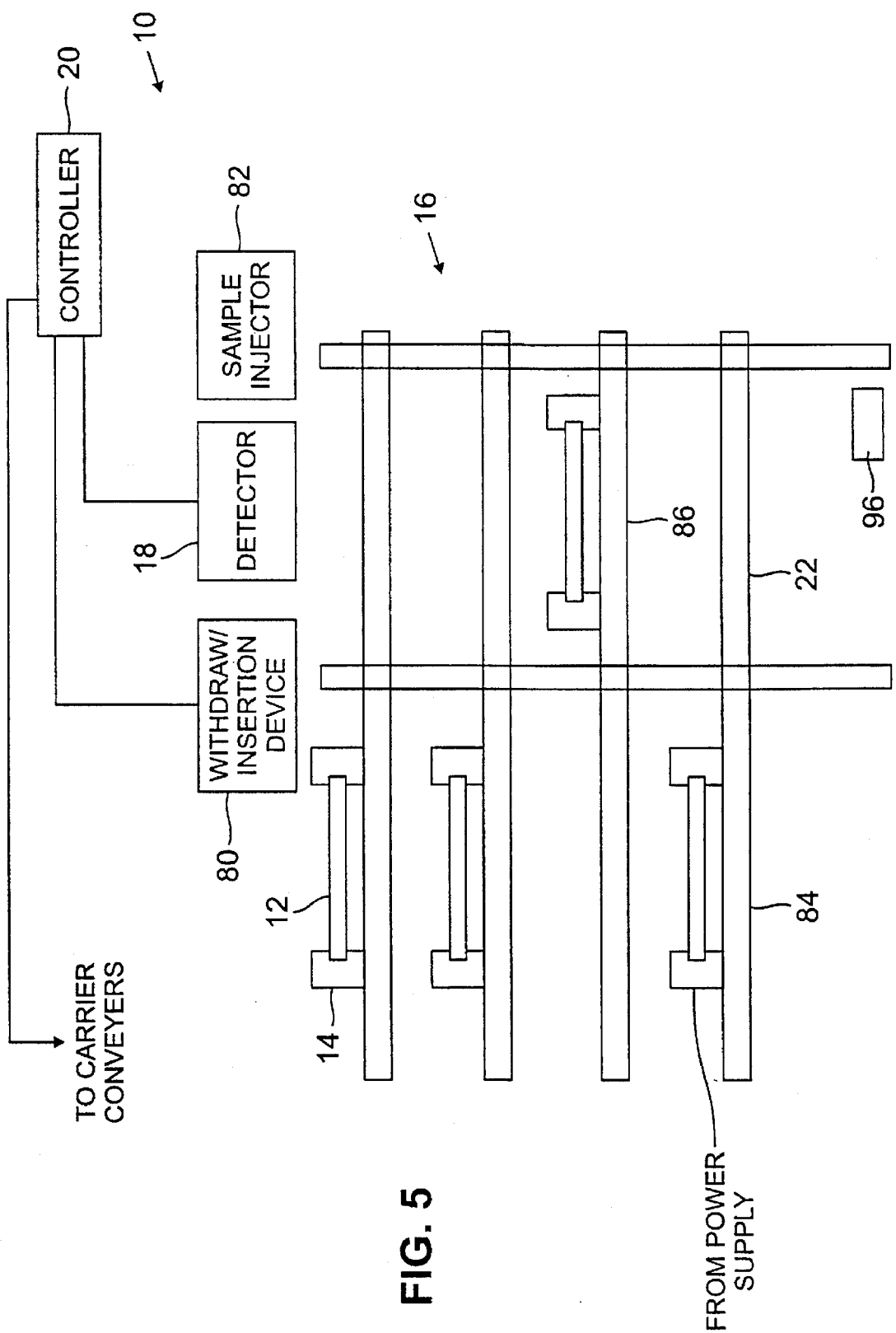
FIG. 5 is a diagrammatic representation of an electrophoresis apparatus according to the invention for simultaneously running a plurality of electrophoresis gels.

Referring to FIG. 5, a system 10 for simultaneously running a plurality of electrophoresis gels 12 is shown (four gels being shown for representative purposes only). Each electrophoresis gel 12 is supported by an electrophoresis gel carrier 14, which may be any of the gel carriers described above in conjunction with FIG. 1–1b, 2–2b, 3–3b and 4–4b. Other well-known gel carriers, for example, the electrophoretic apparatus described by Kambara et al., in U.S. Pat. No. 5,192,412, incorporated herein by reference, may also be used in conjunction with system 10. Moreover, both DNA sequencing as well as non-DNA sequencing gels may be imaged using system 10. System 10 includes a platform 16 for supporting gel carriers 14. A detector 18, for example, a charge coupled device (CCD) camera, a diode array or a laser beam measurement instrument (e.g, a typical optical head used in video laser disks, compact disks, or CD ROM drivers), is positioned with respect to platform 16 to acquire information (e.g., an image of gel 12) and to transmit the information to a data collector/controller 20.

Carriers 14 are movably supported on platform 16 by conveyors 22 which move each of the carriers under detector 18 according to a predetermined sequence selected such that the detector acquires information from each of the gels at known time intervals. Conveyors 22 may be in the form of rails having teeth configured to engage a drive gear from a drive mechanism. Alternatively, conveyor 22 may be driven with a sprocketed chain or belt. The conveyor 22 may be in the form of rails with carriers 14 having wheels which travel along the rails. Step motors connected to the bottom surface of each carrier may be used to power the wheels.

Position sensors (not shown) are employed to sense the position of carriers 14 and send this information to data collector/controller 20 which instructs detector 18 to take an image of a gel.

Figure 6:
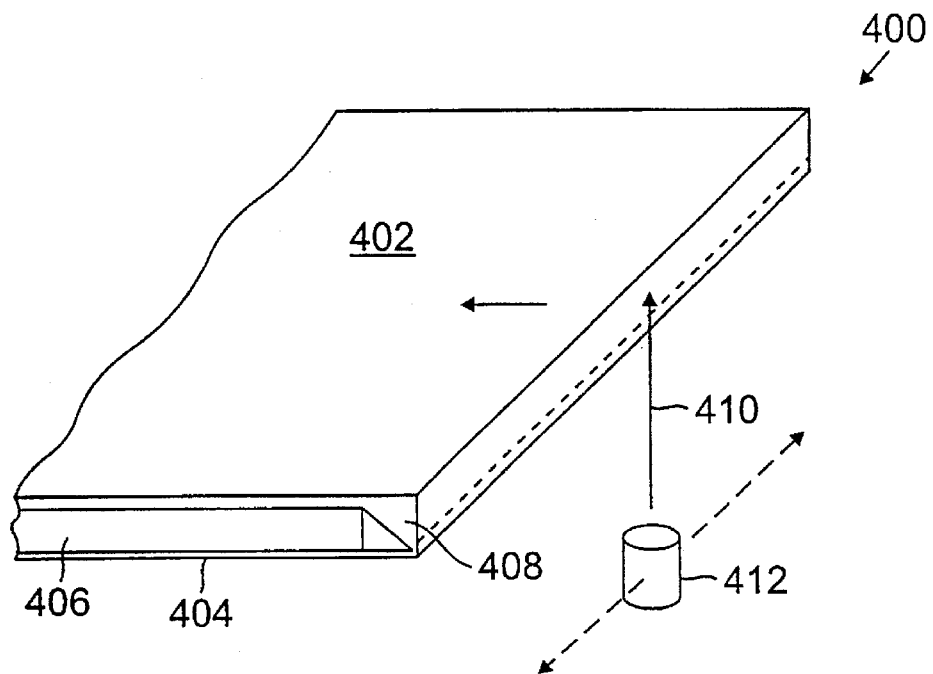
FIG. 6 is a diagrammatic perspective view of a portion of a gel carrier having a reflective mirror.

Referring to FIG. 6, in one embodiment, electrophoresis gel carrier 400 is formed as two overlapping glass plates 402, 404 having an electrophoresis gel 406 disposed therebetween. Upper plate 402 includes a longitudinal reflective mirror 408 positioned along one lateral edge of the carrier to redirect a laser beam 410 emitted from a laser 412. Laser 412 is mounted to a separate conveyor (not shown) positioned at the bottom of platform 16 and under detector 18 to allow the laser to move in one direction (indicated by dashed arrows) along the length of mirror 408. Once gel carrier is moved to imaging position 86, laser beam 410 is scanned across the entire length of the gel. During laser scanning of the gel, detector 18 (e.g., CCD camera) is activated to receive the entire image of the gel. In embodiments where a diode array is used as the detector, the array moves synchronously with the conveyor supporting laser 96. Depending on the structure of the gel carrier (e.g., capillary tubes, slab), light collecting, focusing and steering mechanisms may be used to illuminate the desired area or portion of the electrophoresis gel.

Referring again to FIG. 5, the required voltage to create an electric field to perform electrophoresis is transmitted to carriers 14 via wires 26 from a power source (not shown). Wires 26 may be recoilable to extend and retract as carriers 14 move along the conveyors.

System 10 further includes a withdraw/injection device (represented by box 80) for withdrawing used buffer solution and reinjecting fresh buffer solution. A buffer solution storage tank (not shown) is provided to store the buffer solution. Withdraw/injection device 80 is controlled by data collector/controller 20, with buffer exchange and sample injection taking place when carrier 14 is transferred to imaging position 86. Withdraw/injection device 80 includes a controller, a pump for liquids, and a pair of tubes connecting corresponding tanks holding fresh buffer and used buffer solutions, respectively. The tubes are fixed on distinct machine arms with the pump and arms controlled by controller 20. Withdraw/injection device is used to inject fresh buffer solution (FBS) into buffer wells (56, 256) and well cells (102, 302) when the electroconductivity of the buffer has been exhausted. The electroconductivity is reduced over time and use due to a chemical change in the contents of the buffer. To replace the buffer, the withdraw/injection device 80 extends its arm to dispose the used buffer solution (UBS). The injection arm is then moved to a position to inject the FBS. After the buffer solution has been renewed, carrier 14 is restarted to finish the electrophoresis process. A sample injector (represented by box 82) injects sample solutions into gel carriers 14. For example, a sample injector similar to the GS Gene Loader II, a product of Bio-Rad Laboratories, Hercules, Calif. would be suitable for use with the system.

In operation, under the automatic control of data collector/controller 20, buffer solution and sample solution are added to each gel carrier 14. An electric field is applied across gels 12 and after the electrophoresis process has proceeded for a predetermined time (e.g., five minutes), each carrier 14 is, in turn, moved from a storage position 84 to an imaging position 86 under detector 18. An image of the gel is taken, and the carrier is moved back to storage position 84. At predetermined time intervals (e.g., every five minutes) each carrier is again, in turn, moved under detector 18 and an image of the gel is taken until the electrophoresis process is completed. Data collector/controller 20 is then used to analyze the gel images and provide the desired information (e.g., a DNA sequence).

FIG. 5 illustrates a representative conveyor in which conveyors 22 are in a stacked configuration with the carrier 14 being sequentially horizontally movable from a storage position 84 to an imaging position 86 under detector 18. In the embodiment shown in FIG. 5, it should be noted that as each carrier is moved to its imaging position 86 under detector 18, the distance between the detector 18 and carrier varies. Thus, in this embodiment, it is generally required that either the detector be moved or a focusing mechanism be provided to compensate for the variable distance.

Other conveying means for aligning carriers 14 and detector 18 according to a predetermined sequence can also be employed. Platform 16 may also be configured to allow carriers to be moved both horizontally and vertically to a fixed imaging position. In this embodiment, a fixed focus imaging detector may only be required. Moreover, withdraw/injection device 80 and the sample injector 82 may be positioned to be stationary with respect to the platform. In alternative embodiments of platform 16, detector 18 can be positioned sequentially over each carrier 14 to take an image while the carriers remain stationary, or both the detector and the carriers can be moved. Alternatively, the carriers may be oriented vertically, in a bookshelf manner with each carrier in turn being raised out of the line of gels to have an image taken and then returned to the line of gels according to a predetermined sequence.

Figure 7:
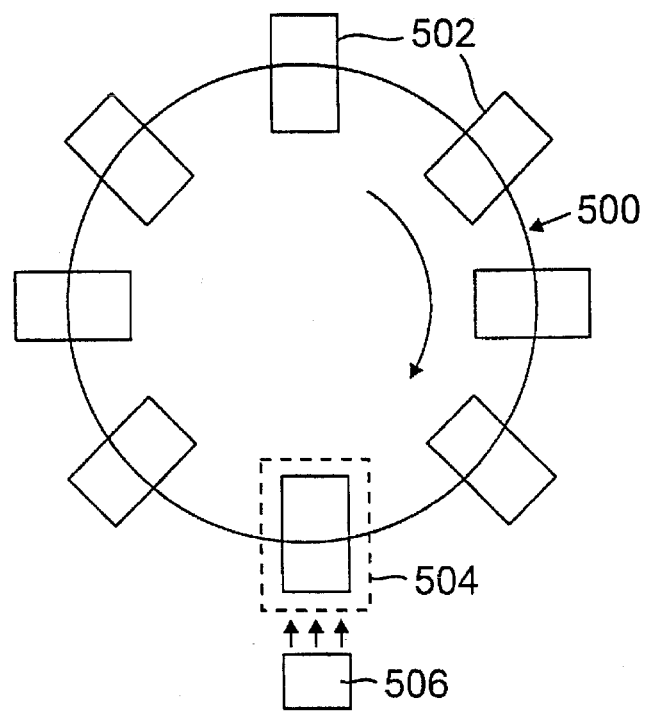
FIG. 7 is a schematic representation of another embodiment of an electrophoresis apparatus according to the invention.

In still other embodiments of platform 16, the carriers may be moved sequentially along a single conveyor which positions the carrier being imaged. The path of the conveyor may take any shape including, for example, carousel shaped. For example, referring to FIG. 7, a conveyor 500 supports eight gel carriers 502. Conveyor 500 moves each carrier 502 to an imaging position 504 where a detector 506 records an image of the gel. Alternatively, in another embodiment, the detector 506 moves around the periphery of a carousel-shaped platform supporting gel carriers at fixed positions.

These and other embodiments of the invention are within the following claims.

For example, laser 412, described above in conjunction with FIG. 6, may be used to illuminate the electrophoresis gel in the same way conventional laser printers are used to scan a line of print over a sheet of paper. The steering beam redirector used in such printers can be used to illuminate portions of a slab or capillary gels. Alternatively, an array of conventional laser beam measurement instruments, each having a laser diode and a beam splitter connected to a detector. The array moves linearly to obtain information from the gels.

Although a light source has been described above, it is to be noted when bioluminescent or chemicalluminescent technology (e.g. deoxyadenosine triphosphate together with luciferase), is employed, the light source may not be needed. Moreover, a conventional ultraviolet light source may be used where the gel is formed and supported by a UV permeable material.

What is claimed is:

1. An apparatus for performing a plurality of electrophoresis processes, comprising:
    a plurality of electrophoresis gel carriers, each carrier supporting an electrophoresis gel and including:
        first and second end mounts, said first end mount for receiving a first end of the electrophoresis medium gel, said second end mount for receiving a second opposite end of the electrophoresis medium gel, wherein at least one of said end mounts includes:
        a base plate defining a lower retainer, and
        an upper retainer aligned and configured to couple with said lower retainer, said lower and upper retainers defining discrete sample well cells, each of said sample well cells receiving one or the other of the first and second ends of the gel,
    a detector configured to acquire information from the electrophoresis gel carriers and transmit the information to a data collector, and
    a conveyor which moves at least one of said detector and said gel carriers with respect to each other to allow said detector to acquire said information from each of said gel carriers in a predetermined sequence, said predetermined sequence selected such that said detector acquires information from each of the electrophoresis gels at known time intervals.

2. The apparatus of claim 1 further comprising a platform adapted to support the plurality of electrophoresis gel carriers.

3. The apparatus of claim 2 wherein each of the gel carriers are supported at stationary positions of said platform and said detector moves to the stationary positions to acquire information from each of the gels.

4. The apparatus of claim 2 wherein said imaging and storage positions are coplanar.

5. The apparatus of claim 1 further including a plurality of resident positions comprising:
    at least one imaging position where said detector, in a predetermined sequence, acquires information from each of the gels;
    a plurality of storage positions where an electrophoresis process is performed and where one of said carriers reside when said information is not being acquired from said one of said carriers; wherein
    said conveyor moves said carriers between said storage positions and said at least one imaging position.

6. The apparatus of claim 5 wherein the conveyor rotates to move each of said carriers from their respective storage positions to said at least one imaging position.

7. The apparatus of claim 1 wherein said carriers contain buffer solution and said apparatus further comprises a buffer withdraw/injection device in communication with a buffer storage tank configured to withdraw used buffer from said carriers and injecting new buffer.

8. The apparatus of claim 1 further including a sample injector configured to add sample to said carriers.

9. The apparatus of claim 1 further including a data collector/controller configured to automatically control said apparatus.

10. The apparatus of claim 1 wherein said detector includes a charge coupled device.

11. The apparatus of claim 1 wherein said lower retainer includes a plurality of lower concave surfaces, and
    said upper retainer plate includes a plurality of upper concave surfaces in alignment with said lower concave surfaces, each of said aligned upper and lower concave surfaces defining an aperture opening into one of said sample well cells,
    said aperture in said first end mount for receiving a first end of said electrophoresis medium gel in the form of a capillary tube, said aperture in said second end mount each for receiving a second end of the capillary tube.

12. The apparatus of claim 1 wherein said electrophoresis medium gel is in the form of a slab and said buffer well in said first mount defines a slot for receiving a first end of said slab, said slot in said second end mount for receiving a second end of said slab, said slab being received such that said ends of said slab communicate with said sample well cells.

13. The apparatus of claim 1 including a reflective mirror, disposed along a lateral edge of said gel, and configured to redirect light from an external source through said gel.

* * * * *